US008512290B2

(12) United States Patent
Rioux et al.

(10) Patent No.: US 8,512,290 B2
(45) Date of Patent: Aug. 20, 2013

(54) DEVICES AND METHODS FOR DELIVERING THERAPEUTIC OR DIAGNOSTIC AGENTS (75) Inventors: Robert Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2691 days.

(21) Appl. No.: 10/392,545

(22) Filed: Mar. 20, 2003

(65) Prior Publication Data

US 2004/0186422 A1  Sep. 23, 2004

(51) Int. Cl.
*A61M 5/178* (2006.01)
*A61M 31/00* (2006.01)

(52) U.S. Cl.
USPC ..................... 604/164.01; 604/506

(58) Field of Classification Search
USPC ........... 604/20–22, 118, 158, 164.01, 164.09, 604/165.01, 165.02; 606/41, 47
See application file for complete search history.

(56) References Cited

U.S. PATENT DOCUMENTS

| | | | |
|---|---|---|---|
| 3,736,939 A | 6/1973 | Taylor | |
| 4,127,133 A | 11/1978 | Martinez | |
| 4,240,433 A * | 12/1980 | Bordow | 604/540 |
| 4,848,344 A | 7/1989 | Sos et al. | |
| 4,935,006 A | 6/1990 | Hasson | |
| 5,066,278 A | 11/1991 | Hirschberg et al. | |
| 5,167,625 A | 12/1992 | Jacobsen et al. | |
| 5,358,792 A | 10/1994 | Mehta et al. | |
| 5,403,311 A | 4/1995 | Abele et al. | |
| 5,458,597 A * | 10/1995 | Edwards et al. | 606/41 |
| 5,500,012 A | 3/1996 | Brucker et al. | |
| 5,522,815 A | 6/1996 | Durgin, Jr. et al. | |
| 5,536,242 A | 7/1996 | Willard et al. | |
| 5,609,629 A | 3/1997 | Fearnot et al. | |
| 5,718,702 A | 2/1998 | Edwards | |
| 5,749,914 A | 5/1998 | Janssen | |
| 5,843,050 A | 12/1998 | Jones et al. | |

(Continued)

FOREIGN PATENT DOCUMENTS

WO WO 00/67647  11/2000
WO WO 01/41656 A1  6/2001

OTHER PUBLICATIONS

Examiners Answers dated Aug. 21, 2007 to Appeal Brief for related U.S. Appl. No. 10/392,545 filed Mar. 20, 2003. Inventor: Robert Rioux (13 pages).

(Continued)

*Primary Examiner* — Kevin C. Sirmons
*Assistant Examiner* — Andrew Gilbert
(74) *Attorney, Agent, or Firm* — Bingham McCutchen LLP (57) ABSTRACT An agent delivery device includes an outer tubular body having a distal end, a proximal end, and a lumen extending between the distal end and the proximal end, an inner tubular body positioned coaxially within the lumen of the outer tubular body, the inner tubular body having a distal end configured for puncturing tissue, a proximal end, and a lumen extending between the distal end and the proximal end of the inner tubular body, and a suction port located at the distal end of the outer tubular body, the suction port being in fluid communication with the lumen of the outer tubular body. The inner tubular body may be fixedly or slidably secured to the outer tubular body. The agent delivery device may further include a monopolar or bipolar electrode and/or a radio-opaque marker carried at the distal end of the device.

18 Claims, 5 Drawing Sheets

(56) References Cited

U.S. PATENT DOCUMENTS

| | | | |
|---|---|---|---|
| 6,010,476 A * | 1/2000 | Saadat | 604/22 |
| 6,106,524 A | 8/2000 | Eggers et al. | |
| 6,179,824 B1 * | 1/2001 | Eggers et al. | 604/500 |
| 6,221,039 B1 | 4/2001 | Durgin et al. | |
| 6,319,230 B1 | 11/2001 | Palasis et al. | |
| 6,461,296 B1 * | 10/2002 | Desai | 600/210 |
| 6,582,423 B1 | 6/2003 | Thapliyal et al. | |
| 6,695,822 B2 | 2/2004 | Adams et al. | |
| 6,770,070 B1 * | 8/2004 | Balbierz | 606/41 |
| 2002/0055712 A1 | 5/2002 | Neracher | |
| 2002/0055729 A1 | 5/2002 | Goll | |
| 2003/0028172 A1 | 2/2003 | Epstein et al. | |
| 2004/0087828 A1 | 5/2004 | Green et al. | |

OTHER PUBLICATIONS

Advisory Action dated Jul. 24, 2007 for related U.S. Appl. No. 10/926,853, filed Aug. 25, 2004, Inventor: Robert Rioux (3 pages).
PCT International Preliminary Report on Patentability for PCT/US2004/003147, Applicant: Boston Scientific Limited et al., Form PCT/IB/326, dated Oct. 6, 2005 (7 pages).
Office Action dated May 14, 2007 for related Application U.S. Appl. No. 10/926,853, filed Aug. 25, 2004, Inventor: Robert F. Rioux (7 pages).
PCT International Search Report for PCT/US2005/029699, Applicant: Boston Scientific Scimed, Inc., Form PCT/ ISA/210 and 220, dated Jul. 5, 2006 (9 pages).
PCT Written Opinion of the International Search Authority for PCT/US2005/029699, Applicant: Boston Scientific Scimed, Inc., Form PCT/ISA/237, dated Jul. 5, 2006 (7 pages).
Final Office Action dated Nov. 30, 2004 from related U.S. Appl. No. 10/392,545 filed Mar. 20, 2003, Inventor: Robert Rioux (7 pages).
Advisory Action dated Feb. 10, 2005 from related U.S. Appl. No. 10/392,545 filed Mar. 20, 2003, Inventor: Robert Rioux (2 pages).
Notification of Non-Compliant Appeal Brief dated Jul. 12, 2005 from related U.S. Appl. No. 101392,545 filed Mar. 20, 2003, Inventor: Robert Rioux (2 pages).
Advisory Action dated Jul. 24, 2007 from related U.S. Appl. No. 10/926,853 filed Aug. 25, 2004, Inventor: Robert Rioux (3 pages).
Office Action dated May 14, 2007 for related U.S. Appl. No. 10/926,853, filed Aug. 25, 2004, Inventor: Robert Rioux (7 pages).
Non-Final Office Action dated Nov. 22, 2006 for related U.S. Appl. No. 10/926,853 filed Aug. 25, 2004, Inventor: Robert Rioux et al. (12 pages).
PCT International Search Report for PCT/US2005/015893, Applicant: Boston Scientific Scimed, Inc., Form PCT/ ISA/210 and 220, dated Jan. 3, 2006 (8 pages).
PCT Written Opinion of the International Search Authority for PCT/US2005/015893, Applicant: Boston Scientific Scimed, Inc., Form PCT/ISA/237, dated Jan. 3, 2006 (5 pages).
Non-Final Office Action dated Sep. 30, 2005 for related U.S. Appl. No. 10/846,476 filed May 13, 2004, Inventor: Robert Rioux (5 pages).
Non-Final Office Action dated Nov. 2, 2005 for related U.S. Appl. No. 10/846.476 filed May 13, 2004, Inventor: Robert Rioux (9 pages).
Final Office Action dated Apr. 18, 2006 for related U.S. Appl. No. 10/846,476 filed May 13, 2004, Inventor: Robert Rioux (9 pages).
Non-Final Office Action dated Oct. 19, 2006 for related U.S. Appl. No. 10/846,476 filed May 13, 2004, Inventor: Robert Rioux (7 pages).
Final Office Action dated Apr. 9, 2007 for related U.S. Appl. No. 10/846,476 filed May 13, 2004, Inventor: Robert Rioux (10 pages).
Advisory Action dated Jun. 28, 2007 for related U.S. Appl. No. 10/846,476 filed May 13, 2004, Inventor: Robert Rioux (3 pages).
Advisory Action dated Aug. 2, 2007 for related U.S. Appl. No. 10.846,476 filed May 13, 2004, Inventor: Robert Rioux (2 pages).
PCT International Search Report for PCT/USO4/003147, Applicant: Scimed Life Systems, Inc., Forms PCT/ISA/210 and 220, datd Jun. 21, 2004 (8 pages).
PCT Written Opinion of the International Search Authority for PCT/US04/003147, Applicant: Scimed Life Systems, Inc., Form PCT/ISA/237, dated Jun. 21, 2004 (5 pages).

* cited by examiner

DEVICES AND METHODS FOR DELIVERING THERAPEUTIC OR DIAGNOSTIC AGENTS

FIELD OF THE INVENTION

The field of the invention relates to medical devices, and more particularly, to apparatus and methods for delivering therapeutic or diagnostic agents to a site within tissue.

BACKGROUND

Medical needles have been used to deliver therapeutic or diagnostic agents to a target site within tissue for treatment or diagnostic purposes. Needles typically have a tubular body for delivering an agent, and a sharp distal tip for puncturing skin and/or other bodily tissues, thereby creating a needle tract through intervening tissues between the skin and the target site.

Before the tip of the needle reaches the target site, i.e., while the needle is penetrating through the generally healthy intervening tissue, there is a risk that the agent may leak out of the distal tip of the needle and into the intervening tissue. Since the agent may be sclerotic, necrotic, and/or toxic to living tissue, if the agent leaks or spreads, it may damage the intervening tissue.

After an agent is delivered to the target site, the needle is typically withdrawn, thereby leaving the created tract in the tissues, which eventually closes up through normal healing. However, before the tract is healed, the agent(s) delivered to the target site may leak into the tract, possibly spreading the agent(s) to surrounding tissue. As discussed previously, since the agent may be toxic to living tissue, allowing the agent to spread may damage the surrounding tissue. For example, when treating a prostate with Ethanol, significant amounts of the infused Ethanol may leak through the needle tract, possibly damaging unintended tissue.

Furthermore, when a needle is used to deliver an agent to a tumor, tumor cells may be released into surrounding tissue simply by perforating the tumor with the needle. For example, tumor cells may migrate into the needle tract and into surrounding healthy tissue through the needle tract. This phenomenon is known as "tract seeding."

Thus, apparatus and methods for delivering an agent to a site while preventing or limiting potential leakage of the agent and/or migration of tumor cells to surrounding tissue would be useful.

SUMMARY OF THE INVENTION

The present invention is directed to apparatus and methods for delivering therapeutic or diagnostic agents to a target site within tissue.

In accordance with one aspect of the present invention, an apparatus is provided that includes an inner tubular body and an outer tubular body. The inner tubular body includes a proximal end, a sharpened distal end, a delivery lumen extending therebetween, and one or more outlet ports on the distal end communicating with the delivery lumen. The one or more outlet ports may include an axial outlet or one or more openings in a side wall of the inner tubular body. Optionally, the distal end of the inner tubular body may include an axial opening communicating with the delivery lumen, an interior surface of the inner tubular body being textured for engaging tissue that enters the axial opening.

The outer tubular body includes a proximal end, a distal end, an aspiration lumen extending therebetween, and one or more aspiration ports on the distal end communicating with the aspiration lumen. The inner tubular body may be slidably received in the outer tubular body such that the distal end of the inner tubular body may be advanced beyond the distal end of the outer tubular member. Optionally, a stop may be provided on one of the inner and outer tubular bodies for limiting advancement of the inner tubular body relative to the outer tubular body.

In a preferred embodiment, the inner tubular member is slidably received in the aspiration lumen of the outer tubular member. The aspiration lumen may include a space between the inner and outer tubular members that extends from the proximal end of the outer tubular member to the one or more aspiration ports. Preferably, the space is an annular space that extends between the proximal and distal ends of the outer tubular member.

Optionally, the apparatus may include a source of agent coupled to the proximal end of the inner tubular body such that the source of agent communicates with the delivery lumen and/or a source of vacuum coupled to the proximal end of the outer tubular body such that the source of vacuum communicates with the aspiration lumen.

In addition, the apparatus may include one or more of the following: an electrode or a radio-opaque marker. For example, one or more electrodes may be provided on at least one of the distal end of the outer tubular body and the distal end of the inner tubular body. A source of electrical energy, e.g., a radio frequency (RF) generator, may be coupled to the electrode(s). In addition or alternatively, a radio-opaque marker may be provided on at least one of the distal end of the outer tubular body and the distal end of the inner tubular body, and preferably on both the inner and outer tubular bodies.

In accordance with another aspect of the present invention, an apparatus is provided that includes an elongate body including a proximal end, and a distal end terminating in a tissue piercing distal tip. A delivery lumen extends from the proximal end to one or more outlet ports adjacent the distal tip, and an aspiration lumen extending from the proximal end to one or more inlet ports on the distal end proximal to the one or more outlet ports;

A source of therapeutic or diagnostic agent may be coupled to the proximal end of the body communicating with the delivery lumen for delivering the agent through the delivery lumen to the one or more outlet ports. In addition or alternatively, a source of vacuum may be coupled to the proximal end of the body communicating with the aspiration lumen for aspirating material adjacent the one or more inlet ports into the aspiration lumen.

In accordance with yet another aspect of the present invention, a method is provided for delivering a therapeutic or diagnostic agent to a target site within tissue. A needle may be advanced through intervening tissue to a target site, thereby creating a tract through the intervening tissue, and a therapeutic or diagnostic agent may be delivered via the needle to the target site. Material, such as excess agent that enters the tract from the target site, may be aspirated. Preferably, material is aspirated from the tract into the needle at a location proximal to one or more outlet ports on the needle used to deliver the agent to the target site. Material may be aspirated from the tract substantially continuously while the needle is within the tract, intermittently, or after the agent is delivered.

Optionally, the tract may be sealed to prevent the agent from leaking substantially from the target site. For example, the tract may be sealed by delivering electrical energy from a portion of the needle to tissue surrounding a least a portion of the tract. The needle may be twisted about its longitudinal axis as it is removed, and, optionally, a short burst of energy may be delivered as the needle is twisted.

In accordance with still another aspect of the present invention, a method is provided for delivering a therapeutic or diagnostic agent to a target site within tissue. An apparatus including inner and outer elongate members may be advanced through intervening tissue until distal ends of the inner and outer members are located adjacent a target site, thereby creating a tract through the intervening tissue. The distal end of the inner member may be advanced into the target site, and a therapeutic or diagnostic agent may be delivered via the inner member into the target site. Material that enters the tract from the target site may be aspirated into the outer member, e.g., substantially continuously, intermittently, and/or after the agent is delivered.

After delivering the agent, the distal end of the inner member may be retracted at least partially into the outer member, and/or the inner and outer members may be removed from the tract. Optionally, the tract may be sealed, e.g., using electrical energy, to prevent the agent from leaking substantially from the target site.

Other aspects and features of the invention will be evident from reading the following detailed description of the preferred embodiments, which are intended to illustrate, but not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not intended to limit its scope, the invention will be described and explained with additional specificity and detail through the use of the accompanying drawings.

DETAILED DESCRIPTION OF THE PREFERRED EMBODIMENTS

Figure 1:
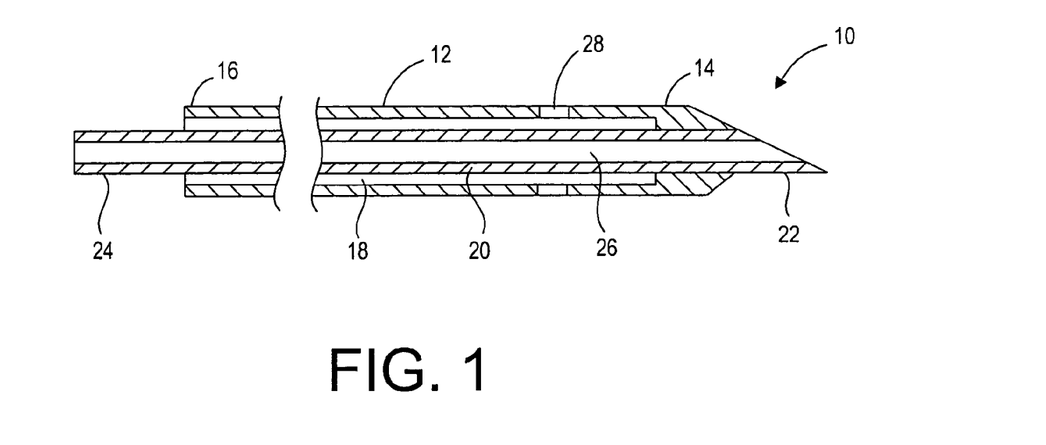
FIG. 1 is a cross-sectional side view of a first embodiment of an apparatus for delivering an agent into tissue, in accordance with the present invention.

FIG. 1 shows an agent delivery device 10 constructed in accordance with an embodiment of the present invention. The agent delivery device 10 includes an outer tubular body 12 having a proximal end 16, a distal end 14, and a lumen 18 extending between the proximal and distal ends 16, 14. The agent delivery device 10 also includes an inner tubular body 20, such as a needle, positioned coaxially within the lumen 18 of the outer tubular body 12. The inner tubular body 20 has a distal end 22, a proximal end 24, and a lumen 26 extending between the distal and the proximal ends 22 and 24. The agent delivery device 10 further includes one or more suction or aspiration ports 28 located at or near the distal end 14 of the outer tubular body 12. The aspiration port 28 will be discussed in further detail below.

The outer tubular body 12 may be made from a variety of materials, such as plastics, polymers, metals, alloys, and graphite. In the illustrated embodiment, the distal end 14 of the outer tubular body 12 has a cross section that is thicker than the rest of the outer tubular body 12, thereby maintaining the inner tubular body 20 substantially coaxially within the lumen 18 of the outer tubular body 12. The proximal end 16 of the outer tubular body 12 is configured to be coupled to a source of vacuum (not shown) that may generate a vacuum within the lumen 18, i.e., within the annular space between the outer tubular body 12 and the inner tubular body 20, that is substantially isolated from the lumen 26 of the inner tubular body 20. Any source of vacuum, e.g., a syringe, a vacuum line, or a pump, may be used, and is generally well known in the art. The aspiration port 28 at or near the distal end 14 of the outer tubular body 12 communicates with the lumen 18 of the outer tubular body 12. When a vacuum is created within the lumen 18 of the outer tubular body 12, fluid or objects outside the outer tubular body 12 may be aspirated into the lumen 18 through the aspiration port 28.

The source of vacuum may be coupled to the proximal end 16 of the outer tubular body 12 using any known manner, e.g., depending on the cross-sectional shape of the outer tubular body 12 and the configuration of the source of vacuum. For example, the proximal end 16 of the outer tubular body 12 may include a connector, e.g., a male or female luer lock connector (not shown), that may substantially seal the lumen 18 at the proximal end of the outer tubular body 12 when connected to the source of vacuum. A section of tubing and the like that communicates with the source of vacuum may include a complementary connector that may engage the connector on the proximal end 16 of the outer tubular member 12. Alternatively, the proximal end 16 of the outer tubular member 12 may be closed, and a nipple or other side port may be provided on the outer tubular member 12 that communicates with the lumen 18. The manner in which the source of vacuum is coupled to the proximal end 16 is not critical to the present invention.

In the illustrated embodiment, the distal end 22 of the inner tubular body 20 may have a tissue piercing tip and/or a low profile that may facilitate penetrating the inner tubular body 20 through skin or other bodily tissues. The proximal end 24 of the inner tubular body 20 is configured to be coupled to a source of therapeutic or diagnostic agent, which may include genetic material and implantable cells as in gene/cell therapy. For example, the proximal end 24 of the inner tubular body 20 may include a connector (not shown) that may be coupled to a syringe, bottle, bag, or other container including the agent therein. Any of the materials discussed previously with reference to the outer tubular body 12 may also be suitable for construction of the inner tubular body 20. It should be understood by those skilled in the art that the flexibility or stiffness of the agent delivery device 10 may be varied by using different materials for the outer and inner tubular bodies 12, 20.

Figure 2:
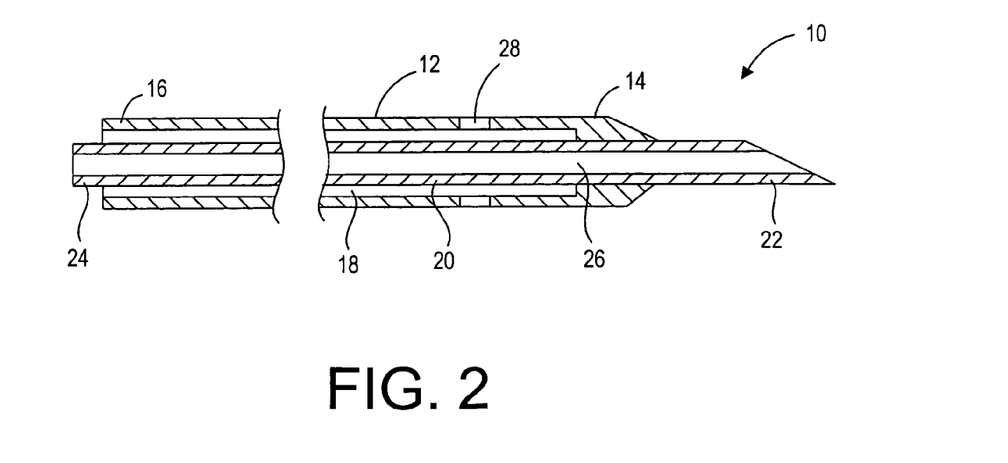
FIG. 2 is a cross-sectional side view of the apparatus of FIG. 1, showing an inner tubular body extending distally relative to an outer tubular body.

The inner tubular body 20 is preferably slidable axially relative to the outer tubular body 12. FIG. 2 shows the inner tubular body 20 advanced distally relative to the outer tubular body 12. The agent delivery device 10 may include a stop (not shown), e.g., secured to the proximal end 24 of the inner tubular body 20 and/or the outer tubular body 12 to prevent the inner tubular body 20 from being advanced beyond a predetermined distance relative to the outer tubular body 12.

Figure 3:
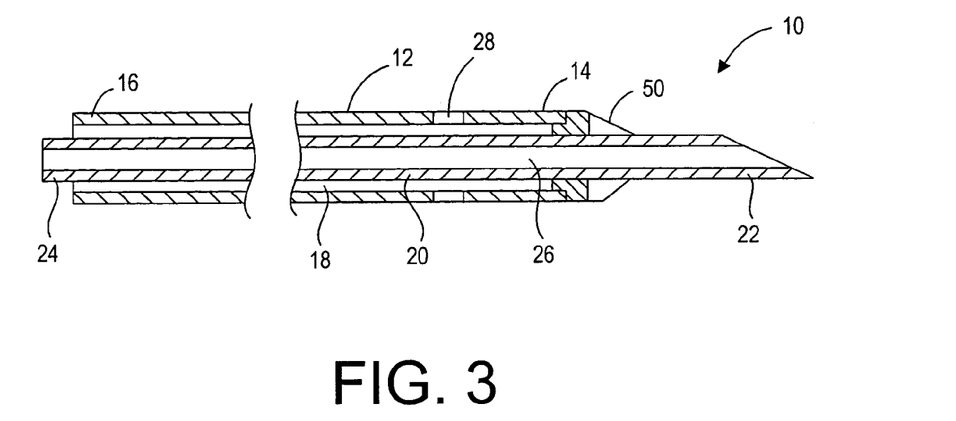
FIG. 3 is a cross-sectional side view of a variation of the apparatus of FIG. 1, showing the apparatus including an electrode carried at its distal end.

As shown in FIG. 3, optionally, the agent delivery device 10 may include one or more electrodes 50 carried at the distal end 14 of the outer tubular body 12. The electrode 50 may be used to treat tissue in a monopolar or bipolar manner, as is known in the art.

Figure 4:
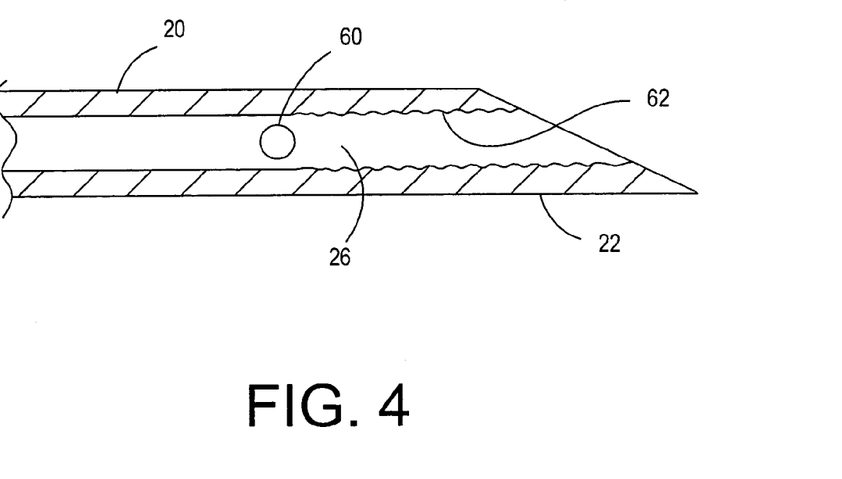
FIG. 4 is a cross-sectional detail of a variation of the apparatus of FIGS. 1 and 2, showing the inner tubular body having a textured interior surface and a side port.

FIG. 4 shows a variation of the inner tubular body 20 that includes one or more delivery ports 60 located along a side wall of the inner tubular body 20. The delivery port(s) 60 is(are) preferably located at or near the distal end 22 of the inner tubular body 20 for delivering an agent therethrough. The delivery port(s) 60 may have different shapes other than the circular shape shown in the illustrated embodiment. For example, the delivery port(s) 60 may have an elliptical shape, rectangular shape, or other customized shape. In addition or alternatively, the interior surface 62 of a distal portion of the lumen 26 of the inner tubular body 20 may be textured (i.e., roughened), which may allow tissue that enters into the distal portion of the lumen 26 to be secured therein and/or retrieved, e.g., while the agent is being delivered through the delivery port(s) 60.

Figure 5:
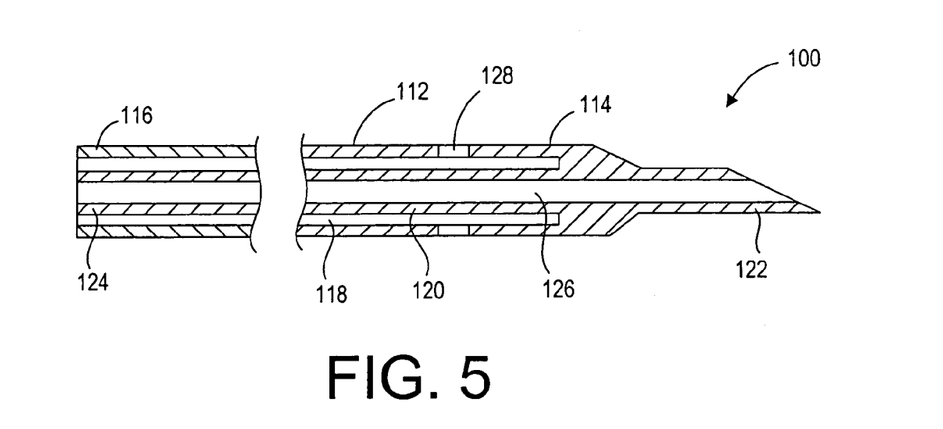
FIG. 5 is a cross-sectional side view of another embodiment of an apparatus, in accordance with the present invention, including an inner tubular body fixedly secured to an outer tubular body.

In the previously described embodiments, the inner tubular body 20 is slidable relative to the outer tubular body 12. However, the scope of the invention should not be so limited. For example, FIG. 5 shows an agent delivery device 100 including an outer tubular body 112 having a proximal end 116, a distal end 114, and a lumen 118 extending therebetween. The agent delivery device 100 also includes an inner tubular body 120 positioned coaxially within the lumen 118 of the outer tubular body 112. The inner tubular body 120 has a distal end 122, a proximal end 124, and a lumen 126 extending between the distal and the proximal ends 122 and 124. The agent delivery device 100 further includes one or more suction ports 128 located at or near the distal end 114 of the outer tubular body 112.

The only difference between the embodiment shown in FIG. 5 and that shown in FIG. 1 is that the inner tubular body 120 is fixed relative to the outer tubular body 112. This may be accomplished using glue, solder, or other suitable adhesive between the outer and inner tubular bodies 112, 120, depending on the materials from which they are made. The outer and inner tubular bodies 112, 120 may also be constructed or mold-formed as a single unit during manufacturing.

As shown in FIG. 5, the distal end 114 of the outer tubular body 112 is secured to the inner tubular body 120 at a location that is proximal to the distal end 122 of the inner tubular body 120. Alternatively, as shown in FIG. 6, the distal end 114 of the outer tubular body 112 may be secured to the distal end 122 of the inner tubular body 112 so that the agent delivery device 100 has a substantially smooth and continuous exterior profile along a length of the agent delivery device 100.

Figure 6:
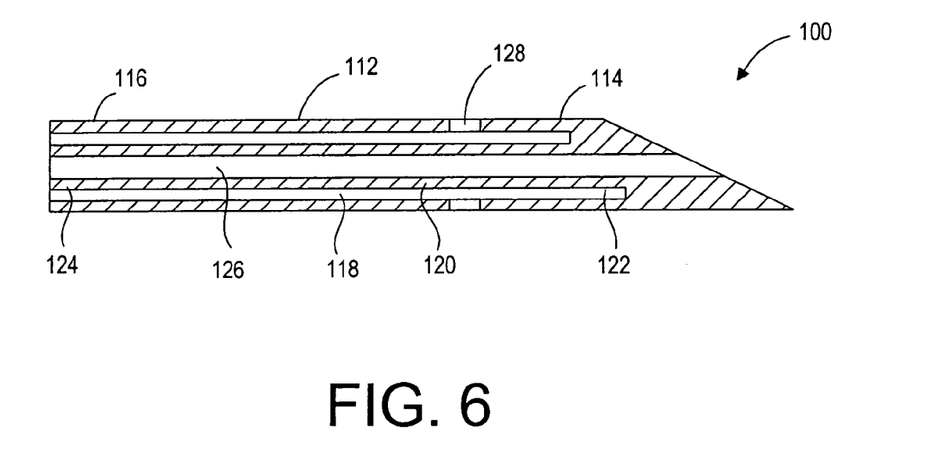
FIG. 6 is a cross-sectional side view of a variation of the apparatus of FIG. 5.

In either of the embodiments shown in FIGS. 5 and 6, the agent delivery device 100 may optionally include one or more electrodes 50, as discussed previously with reference to FIG. 3. Furthermore, the agent delivery device 100 may also include one or more side wall delivery ports 60 and/or a textured interior surface at the distal end 122 of the inner tubular body 120, as discussed previously with reference to FIG. 4.

In any of the embodiments discussed previously, the agent delivery device 10, 100 may include one or more radio-opaque markers carried at the distal end of the agent delivery device 10, 100, such as at the distal end 22 or 122 of the inner tubular body 20, 120, and/or at the distal end 14, 114 of the outer tubular body 12, 112. The radio-opaque marker(s) may assist monitoring the agent delivery device 10 or 100 as it is manipulated or positioned during a procedure, as is known in the art.

Figure 7A:
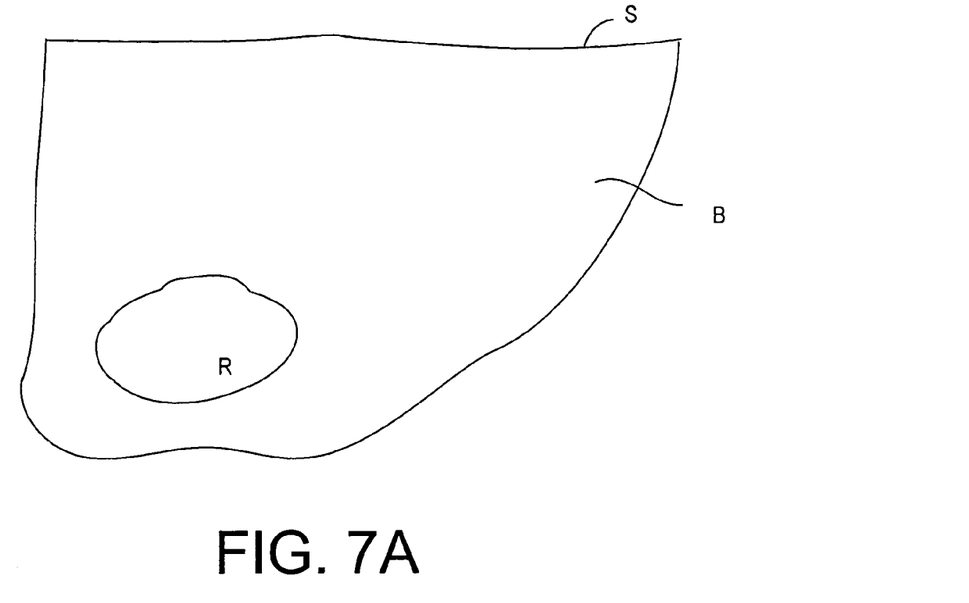
FIGS. 7A-7D are cross-sectional views showing a method for using an apparatus to deliver an agent into tissue.

Referring now to FIGS. 7A-7D, the agent delivery device 10 (or other devices described above) may be used to treat or diagnose a target region R within tissue located beneath the skin S and intervening tissue B of a patient. FIG. 7A shows the region R before the procedure is begun. Before the procedure, the proximal end 24 (not shown) of the inner tubular body 20 may be coupled to a source of agent (also not shown), and/or the proximal end 16 (not shown) of the outer tubular body 12 may be coupled to a source of vacuum (also not shown).

Figure 7B:
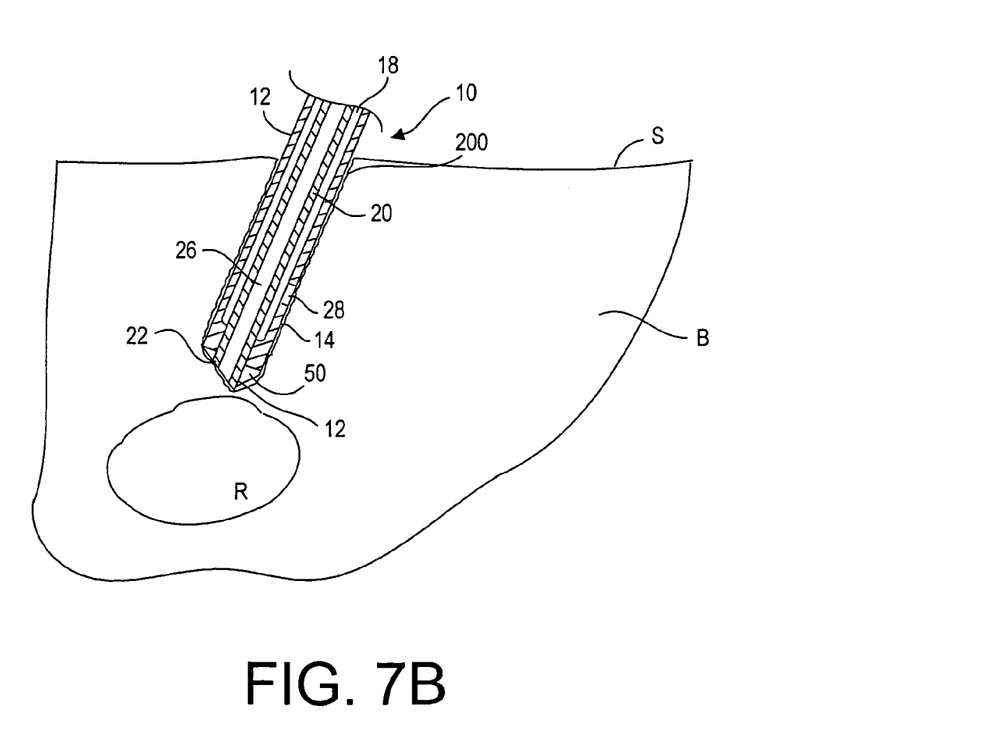

As shown in FIG. 7B, the distal end 22 of the inner tubular member 20 may be retracted at least partially into the distal end 14 of the outer tubular member 12. The device 10 is then advanced through the skin S and intervening tissue B until the distal ends 22, 14 are located adjacent to the region R. Preferably, the sharp distal end 22 of the inner tubular body 20 facilitates penetrating the skin S and intervening tissue B, thereby creating a tract or pathway 200 leading to the region R.

Figure 7C:
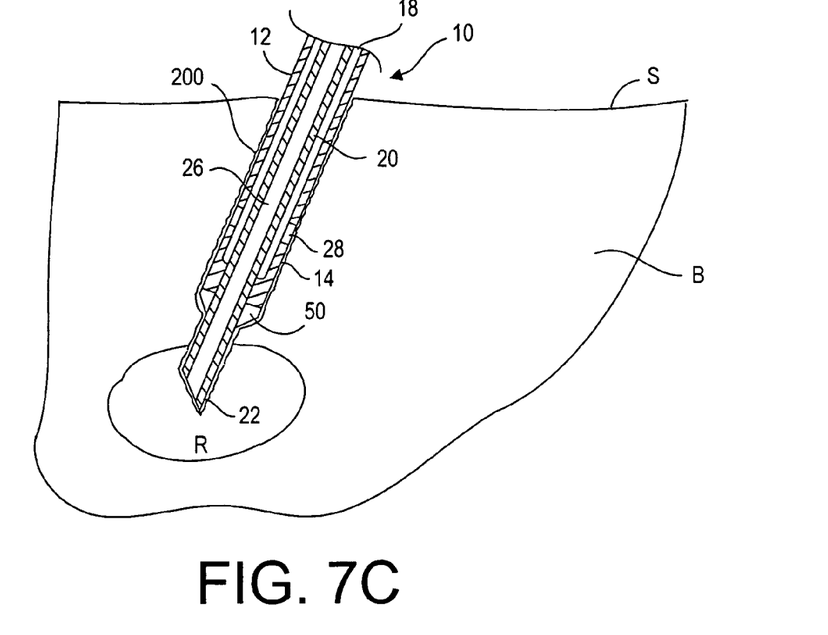

As shown in FIG. 7C, once the distal end 14 of the outer tubular body 12 is positioned adjacent to the region R, the distal end 22 of the inner tubular body 20 is advanced distally into the region R. Alternatively, the distal end 14 of the outer tubular body 12 may be positioned within the region R, and the inner tubular body 20 may be advanced such that the distal end 22 extends further into the region R. If the agent delivery device 10 includes one or more radio-opaque markers, the marker(s) may be used to assist positioning the distal ends 14, 22 of the agent delivery device 10. In a further alternative, if a device 100, such as that shown in FIG. 5 or 6, is used that includes an inner tubular body 120 fixed to an outer tubular body 112, the device 100 may be advanced distally until the distal end 122 reaches the region R. Optionally, as shown in FIG. 4, if the inner tubular body 20 includes a textured interior surface 62, tissue may enter at least partially into the lumen 26 as the inner tubular body 20 is advanced into the region R. This may allow a portion of tissue from the region R to be retrieved, e.g., for a biopsy or other analysis.

Returning to FIG. 7C, once the distal end 22 of the inner tubular body 20 is desirably positioned within the region R, the agent is then delivered into the region R via the lumen 26 and distal end 22 of the inner tubular body 20. If the inner tubular body 20 includes one or more side ports 60, such as that shown in FIG. 4, the agent may exit from the side port(s) 60. As the agent is being delivered into the region R, some of the agent may seep or otherwise leak into the tract 200. If the source of vacuum is not already creating a vacuum within the lumen 18 of the outer tubular body 12, the source may be activated to create a vacuum to aspirate the agent entering the tract 200 into the lumen 18 through the aspiration port(s) 28. Preferably, the source of vacuum is activated before the agent delivery device 10 is inserted into the patient so that any fluid that enters the tract 200 is aspirated. Alternatively, the source of vacuum may be activated at any time during the procedure, e.g., at periodic time intervals.

Figure 7D:
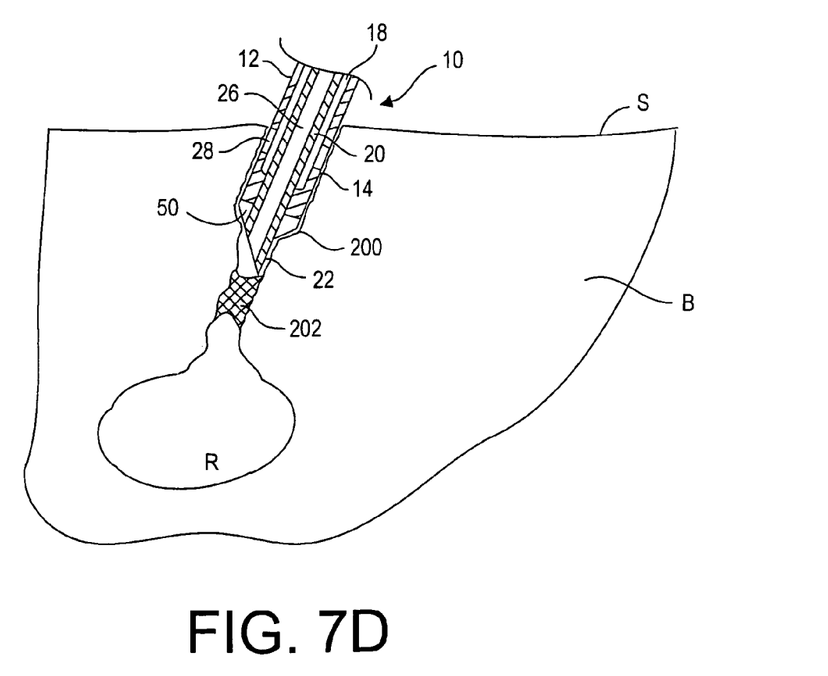

Turning to FIG. 7D, the inner tubular body 20 may be retracted proximally relative to the outer tubular body 12, e.g., to withdraw the distal end 22 of the inner member 20 into the outer tubular member 12. The agent delivery device 10 may then be withdrawn proximally from the tract 200 and the patient. If tissue is captured within the lumen 26 of the inner tubular body 20, it may be separated from the remaining tissue within the region R and removed from the patient as the device 10 is removed.

If the agent delivery device 10 includes one or more electrodes, such as the electrode 50 shown in FIG. 3, energy may be delivered via the electrode(s) 50 to treat the tissue surrounding the tract 200. Preferably, the electrode(s) 50 may deliver radio frequency (RF) electrical energy to coagulate, ablate, or otherwise treat the surrounding tissue to substantially seal or occlude the tract 200. In one embodiment, only the tissue at region 202 adjacent the region R is treated, which should be sufficient to prevent leakage of the agent from the region R and/or migration of tumor cells into the tract 200. Alternatively, energy may be delivered to additional tissue along the tract 200, i.e., to in short bursts such that spaced-apart regions are treated. In another alternative, energy may be delivered substantially continuously as the device 10 is withdrawn to substantially seal the tract 200 along its entire length. Thus, the tract 200 may be substantially sealed, thereby preventing or reducing the risk of track seeding from a tumor and/or contaminating tissue surrounding a target region to which an agent is delivered.

Although several preferred embodiments have been shown and described, it would be apparent to those skilled in the art that many changes and modifications may be made thereunto without the departing from the scope of the invention, which is defined by the following claims and their equivalents.

What is claimed:

1. An apparatus for delivering a therapeutic or diagnostic agent to a target site within tissue, comprising:
    an inner tubular body comprising a proximal end, a tissue piercing distal end, a delivery lumen extending therebetween, and one or more outlet ports on the distal end communicating with the delivery lumen;
    an outer tubular body having a proximal end, a distal end, an aspiration lumen extending therebetween, and one or more aspiration ports on the distal end communicating with the aspiration lumen, the inner tubular body slidably received in the outer tubular body such that the distal end of the inner tubular body is advanceable beyond the distal end of the outer tubular member, wherein the outer tubular body is configured to be percutaneously advanced into the tissue adjacent the target site;
    a source of agent coupled to the proximal end of the inner tubular body such that the source of agent communicates with the delivery lumen; and
    a source of vacuum coupled to the proximal end of the outer tubular body such that the source of vacuum communicates with the aspiration lumen.

2. The apparatus of claim 1, further comprising one or more electrodes on at least one of the distal end of the outer tubular body and the distal end of the inner tubular body.

3. The apparatus of claim 1, further comprising a radio-opaque marker on at least one of the distal end of the outer tubular body and the distal end of the inner tubular body.

4. The apparatus of claim 1, further comprising a stop on one of the inner and outer tubular bodies for limiting advancement of the inner tubular body relative to the outer tubular body.

5. The apparatus of claim 1, wherein the one or more outlet ports comprise one or more openings in a side wall of the inner tubular body.

6. The apparatus of claim 1, wherein the distal end of the inner tubular body comprises an axial opening communicating with the delivery lumen, an interior surface of the inner tubular body being textured for engaging tissue that enters the axial opening.

7. The apparatus of claim 1, wherein the inner tubular member is slidably received in the aspiration lumen of the outer tubular member, the aspiration lumen comprising a space between the inner and outer tubular members that extends from the proximal end of the outer tubular member to the one or more aspiration ports.

8. The apparatus of claim 7, wherein the space comprises an annular space that extends between the proximal and distal ends of the outer tubular member.

9. A method for delivering a therapeutic or diagnostic agent to a target site within tissue, the method comprising:
    advancing a needle through intervening tissue to a target site, thereby creating a tract through the intervening tissue;
    delivering a therapeutic or diagnostic agent via the needle to the target site; and
    aspirating material that enters the tract from the target site.

10. The method of claim 9, further comprising sealing the tract to prevent the agent from leaking substantially from the target site.

11. The method of claim 10, wherein the tract is sealed by delivering electrical energy from a portion of the needle to tissue surrounding a least a portion of the tract.

12. The method of claim 9, wherein material is aspirated from the tract continuously while the needle is within the tract.

13. The method of claim 9, wherein the material is aspirated from the tract into the needle at a location proximal to one or more outlet ports on the needle used to deliver the agent to the target site.

14. The method of claim 12, wherein the material is aspirated from the tract while the therapeutic or diagnostic agent is delivered to the target site.

15. A method for delivering a therapeutic or diagnostic agent to a target site within tissue, the method comprising:
    advancing an apparatus comprising inner and outer elongate members through intervening tissue until distal ends of the inner and outer members are located adjacent a target site, thereby creating a tract through the intervening tissue;
    advancing the distal end of the inner member into the target site;
    delivering a therapeutic or diagnostic agent via the inner member into the target site; and
    aspirating material that enters the tract from the target site into the outer member.

16. The method of claim 15, further comprising sealing the tract to prevent the agent from leaking substantially from the target site.

17. The method of claim 16, wherein the tract is sealed by delivering energy to the intervening tissue adjacent to the target site.

18. The method of claim 16, wherein the tract is sealed by delivering energy from at least one of the inner and outer members to the intervening tissue as the inner and outer members are removed from the tract.

* * * * *